United States Patent [19]

Vilsmeier

[11] Patent Number: 5,769,861
[45] Date of Patent: Jun. 23, 1998

[54] METHOD AND DEVICES FOR LOCALIZING AN INSTRUMENT

[75] Inventor: Stefan Vilsmeier, Poing, Germany

[73] Assignee: Brainlab Med. Computersysteme GmbH, Heimstatten, Germany

[21] Appl. No.: 713,212

[22] Filed: Sep. 12, 1996

[30] Foreign Application Priority Data

Sep. 28, 1995 [DE] Germany .......................... 195 36 180.6

[51] Int. Cl.$^6$ ....................................................... A61B 6/00
[52] U.S. Cl. .............................................. 606/130; 606/73
[58] Field of Search ........................................ 606/130, 73

[56] References Cited

U.S. PATENT DOCUMENTS 5,309,913  5/1994  Kormos et al. ........................... 606/130
5,397,329  3/1995  Allen ........................................ 606/130

OTHER PUBLICATIONS

"Computerized Medical Imaging and Graphics", vol. 18, No. 4, 1994.
"A frameless sterotactic approach to neurosurgical planning based on retrospective patient–imaging registration", J. Neurosurg 79, 296–303, 1993.

Primary Examiner—Michael Powell Buiz
Assistant Examiner—Julian W. Woo
Attorney, Agent, or Firm—Renner, Otto, Boisselle & Sklar, P.L.L.

[57] ABSTRACT

The invention relates to a method of localizing an instrument relative to three-dimensional corporeal data, particularly for stereotaxis, comprising the following steps: connecting internal markers fixedly to the body to define an intracorporeal, spatial reference system, implementing an analytical scan of the body including the internal markers to determine the positions of the three-dimensional corporeal data obtained from analytical scan in the intracorporeal reference system defined by the internal markers, implementing a referencing step, whereby position and orientation of the intracorporeal reference system defined by the internal markers relative to an extracorporeal reference system defined by external markers is determined and said external markers is located outside of the body in a fixed spatial relationship, determining the position and orientation of an instrument in the extracorporeal reference system with the aid of the external markers and a instrument markers attached to the instrument, and computing from said position and orientation in the extracorporeal reference system the position and orientation of the instrument in the intracorporeal reference system via the relationship between the intracorporeal and the extracorporeal reference systems known from the referencing step, as well as a markers device and a device for referencing.

22 Claims, 2 Drawing Sheets

METHOD AND DEVICES FOR LOCALIZING AN INSTRUMENT

BACKGROUND OF THE INVENTION

1. Field of the Invention

The invention relates to a method and devices for localizing an instrument relative to three-dimensional corporeal data and a marker device for defining a corporeal reference system.

The method according to the invention, the marker device according to the invention and the referencing device find application especially in stereotaxis or stereotactic surgery and in other orthopedical or neurosurgical operations, e.g. on the vertebral column.

2. Description of the Prior Art

To localize e.g. the position of a brain tumor three-dimensional scanning of the human brain e.g. by means of computer tomography (CT) or nuclear magnetic resonance (NMR) tomography is applied. In brain surgery, e.g. in removing a tumor, it is necessary to know the precise position of the instrument relative to the tumor. For this purpose stereotactic methods are put to use.

In conventional stereotactic operations a stereotactic instrument is used. This instrument includes a frame which is screwed to the skull. Provided on this frame is a bow which is draw over the skull of the patient. Slidingly secured to this bow is the instrument so that the orientation of the instrument is altered relative to the skull. From this orientation and the depth of penetration of the instrument the position of the instrument tip in the skull can be determined. This position can then be combined with the data obtained from the computer tomography or nuclear magnetic resonance tomography so as to pin-point the position of the tumor as accurately as possible.

So that a fixed relationship is produced between the stereotactic instrument and the data obtained from the three-dimensional analytical scan, it is necessary to firmly screw the frame to the head of the patient prior to the analytical scan, i.e. prior to the CT or NMR tomography. Since this frame is relatively heavy and a rigid connection to the head needs to be assured, it must be firmly anchored in the skull. This is painful, however, for the patient. On top of this this frame needs to be worn by the patient not only during the analytical scan but up until the operation. In conclusion the stereotactic instrument disturbs the three-dimensional analytical scan and obstructs surgery. In addition, it is relatively tiresome to steer to a predetermined point in the brain of the patient by means of the stereotactic instrument which prolongs the duration of the operation.

To overcome these disadvantages so-called frameless stereotactic methods have been proposed and put into practice. Various such methods are known e.g. from "Computerized Medical Imaging and Graphics", Vol. 18, No. 4, 1994. These make use of e.g. anatomic landmarks such as the root of the nose or bone sutures, screws implanted in the skull, protruding from the head, or marker dots bonded to the head. Establishing the position of the marker dot in space or the "teach in" as it is called, is then implemented e.g. by means of a robotic arm. The position of the tip of the robotic arm is calculated from the twists or movements of the joints of the robotic arm and the aforementioned markers are steered to by the robotic arm to sense the positions of the markers by means of a program. The operation is then done by connecting an instrument to the tip of the robotic arm and by determining the position of the instrument tip relative to the tip of the robotic arm. Accordingly, the position of the instrument tip can be related to the data obtained from the analytical scan and e.g. the location of the instrument tip relative to the markers along with the data previously obtained from the three-dimensional analytical scan may be displayed on a screen.

The drawback in using anatomical landmarks, however, is that these are blurred and a "teach-in" without perforating the skin is possible only to a very inadequate degree. Implanted screws have the disadvantage that they need to remain in place in the skull from the time of the analytical scan until the end of the operation. This is a nuisance for totally disinfecting the skull prior to the operation and thus aggravates the risk of infection during the operation. Bonding marker dots to the skin has, in conclusion, the disadvantage that the skin may shift in position relative to the skull between the analytical scan and the operation, i.e. only a very inaccurate determination of the position of the instrument relative to the data obtained from the analytical scan is possible.

To avoid having to apply markers a further method is known from "A frameless stereotactic approach to neurosurgical planning based on retrospective patient-image registration", J. Neurosurg 79, 296-303, 1993. Here, a three-dimensional model of the head surface is stored in a computer. However, here too, accuracies of only 3 to 8 mm typically are achieved due to possible shifts in the skin.

SUMMARY OF THE INVENTION

The object of the invention is to provide a method and devices for precisely localizing an instrument relative to three-dimensional corporeal data obtained by means of analytical scanning whilst simultaneously minimizing the risk of infection and stress on the patient.

This object is achieved by the subject matters of the independent claims.

The sub-claims define expedient embodiments of the invention.

In accordance with the invention a method of localizing an instrument relative to three-dimensional corporeal data is provided. This method may be used e.g. for stereotactic operations, it can, however, also be put to use in any other operations on the human or animal body, particularly in the case of orthopedical or neurosurgical operations. The three-dimensional corporeal data is obtained by means of analytical scanning, i.e. for instance by means of computer tomography (CT) and/or nuclear magnetic resonance (NMR) tomography.

According to the method of the invention an internal marker means is implanted in the body.

This is done to advantage so that the internal marker means is located subcutaneously and preferably secured to the skeleton, e.g. the skull. Such a securement may be made e.g. by introducing a threaded blind hole in the skeleton or by simply screwing the marker into the bone e.g. by means of a cortical screw.

Due to the markers being implanted subcutaneously prior to analytically scanning the body, e.g. the head by e.g. CT, disinfecting the part of the body to be operated prior to the operation is possible with no problem.

Advantageously, the internal markers of the internal marker means are configured small and globular, this permitting, on the one hand, a precise positional determination of the markers in analytical scanning and, on the other, surgery of the body is minimized so that the markers may be implanted under local anaesthesia without stressing the patient particularly.

Due to the markers being implanted in the body, i.e. fixedly secured thereto, it is possible in implementing analytical scanning to produce a CT image and an NMR image one after the other and to combine the data obtained thereby, since by suitably selecting the marker means the marker can be verified both in computer tomography and in nuclear magnetic resonance tomography. The data thereby attained can thus be combined to obtain the three-dimensional corporeal data of the analytical scan.

As a suitable material titanium is used preferably, it also being possible, however, to combine the markers out of different materials which ensure either an optimum demonstration for nuclear magnetic resonance tomography or computer tomography. If other analytical scanning techniques are employed, the markers are made of materials optimally suited to advantage.

At least three markers are used in a known relative position to each other to define a three-dimensional intracorporeal reference system. But, of course, more markers may be used to facilitate a correlation to the extracorporeal reference system to be described below and to minimize errors in determining the position of the markers by the use of several marker position data, e.g. according to the least squares method.

Also of advantage in implanting an internal marker means subcutaneously is that this marker means can also be carried around by the patient with no problem following the operation. This means that in subsequent examinations the success of the operation can be precisely monitored, since the measurement data obtained from the subsequent examination can be precisely correlated to the measurement data obtained prior to the operation. Implanting the marker means thus permits precise tracing of the case history of the patient and in particular the precise observation of the further development in the disease, i.e. the development of a tumor, for instance.

As an alternative to totally implanting the internal marker means subcutaneously only an anchoring for the internal marker means in the skeleton may be implanted subcutaneously, for example. A means for mounting a marker means is then releasably secured in the anchoring when required. Thus, a material suitable for every type of analytical scanning examination may then be selected flexibly.

Furthermore, the mounting means can be removed from the anchoring after the examination. This means that in this case-too, a thorough disinfection of the part of the body to be operated is possible prior to the operation, since the anchoring is implanted totally subcutaneously. After disinfection and prior to the operation the insert provided for the anchoring, comprising the mounting means and the marker means, is then resecured to the anchoring to advantage by latching means. In this arrangement the marker means reattains the same position relative to the skeleton as during the analytical scan.

After implantation of an internal marker means an analytical scan of the body including the internal marker means is implemented, as already described above. The position of the three-dimensional corporeal data obtained by analytical scanning is determined relative to the intracorporeal marker positions e.g. with the aid of a computer and suitable software. As a result of this for instance the location and the extent of a tumor in the reference system established by the internal marker means is determined.

In the next step, termed the referencing step, the position and orientation of an extracorporeal reference system relative to the intracorporeal reference system is determined by determining the position of external markers of an external marker means to make a coordinate transformation possible between the two reference systems. In this arrangement the external marker means is maintained in a fixed spatial relationship to the internal marker means. This is the reason why this step is advantageously made prior to the operation, but after the part of the body to be operated has been fixed.

Such a referencing step may be implemented e.g. by the internal markers being configured as anchorings into which an insert is secured preferably releasably and latching from without through the skin. This insert protrudes from the skin and includes outside of the body an external marker means. By securing the external marker means via the mounting means to the internal marker means, a fixed spatial relationship between the external and internal marker means is produced which is determined and determinable by the type of components used. In this case even a fixing of the part of the body to be operated is dispensable.

As an alternative the referencing step may include a further scan which in the following is termed referencing scan. By means of this referencing scan a direct mechanical connection between the internal and external marker means can be avoided and the relative relationship between an intracorporeal and an extracorporeal reference system nevertheless determined.

For this purpose the external marker means includes to advantage two marker means, namely a first external marker means and a second external marker means. The first external marker means is configured that it can be scanned together with the internal marker means by means of the referencing scan. Thus a relationship is determined between a first external reference system, defined by the first external marker means, and the intracorporeal reference system. Between the second external marker means and the first external marker means a fixed mechanical relationship is produced to advantage which permits conversion of the data, which are transformed into the first extracorporeal reference system into the second external reference system which is defined by the second external marker means.

The second external marker means is configured so that the second external reference system connected thereto can easily be sensed by an instrument position determining means. The method regarding determining the instrument position will be explained in more detail further below.

Contemplatable now is to determine the markers of the first external marker means together with the markers of the internal marker means in turn by a three-dimensional scan such as e.g. by computer tomography. It is of advantage, however, when x-ray images are made from at least two different directions to determine the position of the internal markers relative to the first external markers. It is thus possible e.g. by means of a mobile and rotatable C-bow to determine the position of the internal markers relative to the external markers shortly before the operation or also whilst the operation is going on when the corporeal data to be operated is already fixed. The C-bow can be simply returned out of the way after the determination has been made, so that it is no obstacle to the operation.

In this arrangement the external marker means is configured to advantage so that at least three marker positions can be sensed for each x-ray image. Although it is principally sufficient when all-in-all three marker positions are sensed by all x-ray images, however, the orientation or direction in x-ray imaging relative to the external marker means must be precisely known. If, however, at least three marker positions are determined in each case, which to advantage are not located in a single plane and the position relative to each other is known, then the direction in x-ray imaging made can be computed therefrom. To determine this direction in x-ray imaging as accurately as possible, external markers of the first external marker means are thus provided to advantage before and behind the part of the body to be examined which are sensed in the x-ray images.

As already mentioned above, two x-ray images in differing directions are sufficient to compute therefrom the spatial position of the internal markers relative to the external markers, e.g. by means of suitable software. In this way a precise transformation of the corporeal data obtained by analytical scanning from the internal reference system into the first external reference system is possible.

It is of advantage when the first external marker means and the second external marker means are connected by a spacer which is not a disturbance to the x-ray images. For this purpose e.g. the first external markers are encapsulated in resinous material sold under the trademark PLEXIGLAS and the second external markers are then applied to the resinous material.

Once, as described above, a relationship has been produced between the internal reference system and the extracorporeal reference system, then in a next step the location of the instrument in the intracorporeal reference system is determined. This may be done by conventional means by scanning the positions of the external markers and the position of the instrument as is described e.g. in "Computerized Medical Imaging and Graphics", Vol. 18, No. 4. Also known is the use of ultrasound emitters as markers and the attachment of ultrasound emitters to the instrument.

In addition to these active markers, such as e.g. infrared LEDs or ultrasound emitters, passive markers may also be used preferably.

Preferably passive markers configured as reflectors are employed which reflect infra-red radiation. This infra-red radiation is emitted by the instrument-position-determining means preferably in the form of infra-red flashes. The reflected infra-red beams are detected by three infra-red cameras. From the signals the position of the instrument is determined. For this purpose use is made of the known position of the external markers relative to each other.

One advantage of these passive markers is that the instrument does not require a power supply and thus no leakage current occurs and that it can be moved totally independently of any power leads. This facilitates handling and disinfection of the instrument used.

The drawback in using magnetic fields for determining the position of the instrument is that all other medical instruments need to be shielded and that the determination is relatively inaccurate. When using ultrasound, measurement errors may materialize due to differences in temperature between emitter and detector.

Preferably at least two markers are attached to the instrument to determine the inclination of the instrument. The spacing between the instrument tip and the markers is known. If the instrument tip is e.g. cranked then at least three markers are attached to the instrument so as to determine not only the orientation but also the rotation of the instrument. This in turn makes it possible to compute the position of the instrument tip.

It is of advantage to make use of reflection markers having a ball-shaped surface as large as possible since in optical sensing of the reflection balls by the infra-red cameras computation is made on the basis of the sensed circumference of the reflection balls in obtaining their center point in each case.

To determine on which side of the instrument the instrument tip is located when employing e.g. only two markers on the instrument, a calibration may be undertaken at the start of the operation by e.g. the operating surgeon holding the instrument aimed at the patient. From then on the movement of the instrument is traced and the position of the instrument tip determined. Markers differing in shape and size or having differing reflection properties e.g. as regards the reflected wavelength or the reflected intensity may also be employed, to show in which direction the instrument is pointing by comparing the two different markers.

Once the position of the instrument tip is then finally established in the second external reference system with the aid of the instrument position determining means, then the position of the instrument tip can be determined relative to the corporeal data obtained from the analytical scan with the aid of coordinate transformations.

Accordingly, with the aid of computers and suitable software the position and orientation of the instrument tip can be imaged for an operating surgeon e.g. in 3D relative to the corporeal data, i.e. relative to e.g. the tumor, on a screen in real time.

The accuracy in determining the position of the instrument tip relative to the three-dimensional corporeal data achievable by the method as described above and with the aid of the devices as described above is of the order of 0.1 mm. The method according to the invention is thus considerably more precise than methods known hitherto. In addition, less stress is involved for the patient. The risk of infection is minimized. In conclusion, the work of the operating surgeon is facilitated since the localization method according to the invention is less of an obstruction to him.

The work of the operating surgeon can be further facilitated by after having achieved a reference between the internal and external marker means (first and second external marker means) a further reference is made to a third external marker means. This is of advantage when this third external marker means has a configuration similar to that of the second external marker means.

The third external marker means may be located remotely from the first and second external marker means and thus outside of the operating area. Referencing may be done e.g. again by optical means with the aid of an instrument position determining means. Once referencing as been done and the part of the body to be operated fixed, the first and second marker means can be removed to further facilitate access to the operating area.

Also the third external marker means may be attached to the part of the body to be operated e.g. by bonding, clamping or by means of a hood. This makes it possible for the part of the body to be operated, e.g. the head, to be moved during the operation, since any change in the position and orientation of the third external marker means is continuously sensed by the instrument position determining means.

BRIEF DESCRIPTION OF THE DRAWINGS

Further features and advantages of the invention will be appreciated from the following more detained description of example embodiments on the basis of the drawing in which.

Like reference numerals used in the following identify like parts or parts having like functions.

DESCRIPTION OF THE PREFERRED EMBODIMENTS

Figure 1:
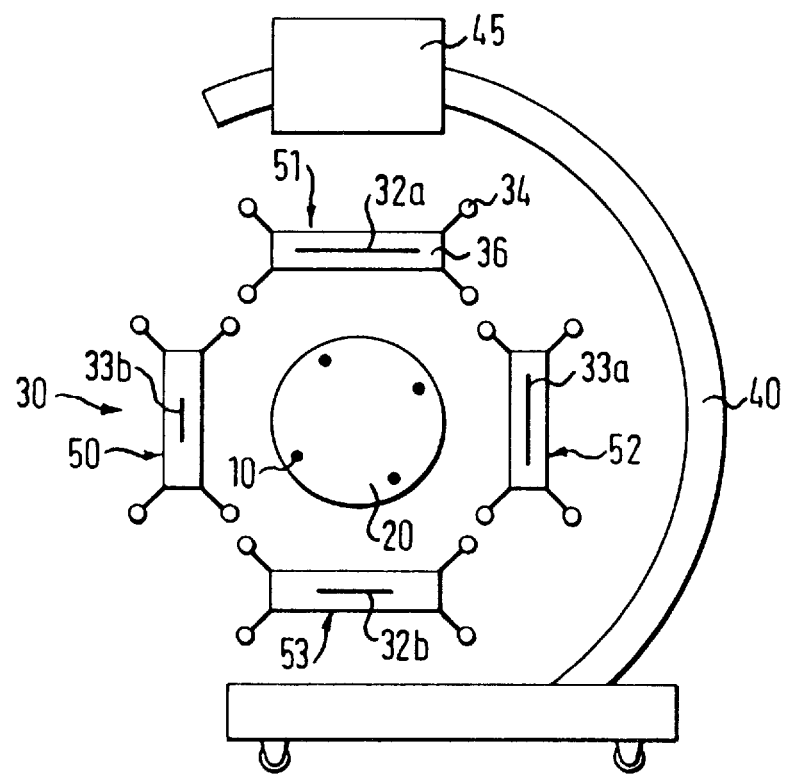
FIG. 1 is a schematic view of a device for referencing the internal reference system to the external reference system with the aid of a C-bow.

In FIG. 1 a device for referencing the intracorporeal reference system to the extracorporeal reference system is shown. The part of the body 20 to be examined, e.g. the head of a patient, is shown in cross-section and represented by a circle in which internal markers 10 are implanted. Outside of the head 20 is the external marker means 30. This comprises four parts 50, 51, 52, 53 of which one is arranged above (51), one below (53) and two (50, 52) on both sides of the head opposite each other, each angularly offset by approx. 90° to each other around the head. Each of these parts includes a copper grid 32, 33 (first external marker means) which is e.g. cut from a sheet of copper by means of a water jet. The copper grid 32, 33 is encapsulated in a block 36 made out of resinous material sold under the trademark PLEXIGLAS (spacer). It is arranged so that the four corners of the copper grid included in the scan of an x-ray image together with the internal markers. According to FIG. 1 part 50 comprises the copper grid 33b, part 51 comprises the copper grid 32a, part 52 comprises the copper grid 33a and part 53 comprises the copper grid 32b.

The head is fixed e.g. by means of a Mayfield adapter (not shown) prior to x-ray imaging to ensure a fixed spatial relationship between the internal and external markers.

The x-ray image is made by means of a C-bow 40, the x-ray apparatus 45 of which is movable along the periphery of the part of the body to be examined. In the position shown in FIG. 1 the x-ray image scans both the copper grid 32a and the copper grid 32b located behind the part of the body to be examined in the direction of the x-ray image. The copper grids 32a and 32b are preferably different in size so that their corner points do not overlap in the x-ray image. For the second x-ray image the x-ray apparatus 45 is travelled along the C-bow 40, e.g. by 90° to x-ray the part of the body to be examined so that the copper grids 33a and 33b are included in the image.

The first external marker means, which according to the example embodiment is formed by copper grids, is preferably connected to the second external marker means by a spacer mounting means which is transparent for x-ray imaging. In this case these are blocks of resinous material sold under the trademark PLEXIGLAS.

Attached to this spacer mounting means is the second external marker means preferably in a known spatial arrangement. When the first external marker means is made up of several parts, e.g. four 32a, 32b, 33a, 33b, as is the case in the example embodiment, then preferably each part is assigned a second external marker means having a fixed spatial relationship to the part concerned. For this purpose in the example embodiment of FIG. 1 four marker balls 34 in each case are fixedly connected to the blocks 36 as the second external marker means. In this way it is possible to bring each individual block an thus the copper grids contained therein into a specific position variably and to then determine this position individually with the aid of the instrument position determining means on the basis of the markers 34 for each block and for each copper grid respectively. This permits adapting the arrangement of the external marker means suitable for the position in each case.

As an alternative, of course, the blocks may be related to each other in a rigid spatial relationship by arranging them on e.g. a ring. In this case it is sufficient to connect at least three markers of the second external marker means to the ring or the blocks.

Figure 2:
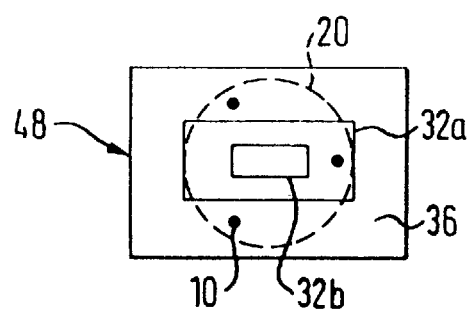
FIG. 2 is a schematic illustration of an x-ray image obtained from a reference scan.

FIG. 2 shows schematically an x-ray image obtained in the reference system. The dashed line indicates the contour of the part of the body 20 to be examined. The internal markers 10 are depicted as dots. In the x-ray image 48 the two copper grids 32a and 32b are evident. For evaluation the corner points of the copper grids 32a and 32b are used. From the position of the corner points of the copper grid 32 relative to the corner points of the copper grid 32b the direction in which the x-ray image is made can be computed. This direction is then included in the evaluation of the x-ray images made in two directions in determining the position of the corner points of the copper grids relative to the internal markers. The two imaging directions are preferably perpendicular to each other.

The position of the corner points of the copper grids relative to the positions of the markers 34 assigned to each block is defined. As a result of this, with the aid of the instrument position determining means the position of each corner point of each and every copper grid 32 can be determined in the operating theater. When markers are suitably attached to the instrument, the position of the instrument tip can be determined in the operating theater. Accordingly, sufficient information is available to compute by means of coordinate transformations the position of the instrument tip relative to the corporeal data obtained from the analytical scan.

If passive markers are used, an instrument position determining means on the basis of an infra-red imaging technique is preferably made use of. This emits preferably emitting infra-red flashes which are reflected by the markers 34. The reflection is registered by at least three infra-red cameras to permit computing the position of the markers. The markers 34 are preferably globular or ball-shaped and have a diameter of e.g. 15 mm.

Figure 3:
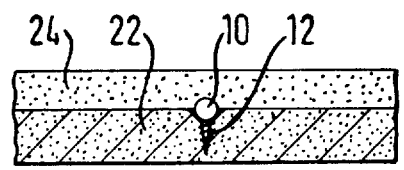
FIG. 3 is a schematic illustration of an implanted marker.

FIG. 3 shows an implanted marker 10 having a threaded fitting 12. This threaded fitting 12 is screwed into a bone 22. The marker 10 is located under the skin 24 and is screwed into place with the aid of a minor incision in the bone 22 under local anaesthesia.

Figure 4:
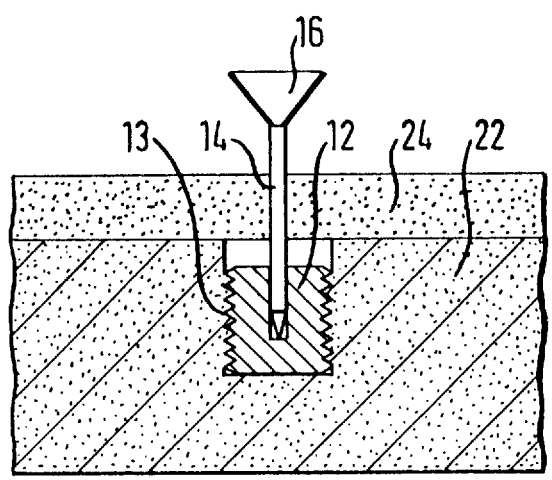
FIG. 4 is a schematic illustration of a marker device having a releasable insert and an anchoring means.

FIG. 4 shows a marker means comprising an anchoring means 12 including a cylindrical shank and an insert 14, 16. The anchoring means 12 is secured to the skeleton bone 22 e.g. by means of a thread 13 beneath the skin 24. It is made of e.g. titanium, carbon fiber or ceramics.

The anchor 12 may then be configured optionally as a marker or serve exclusively as an anchor. If it is configured as a marker it may be made e.g. of titanium. Optionally (not shown) the anchor 12 may be fixedly connected to a marker ball. In the anchor 12 a needle-shaped mounting means 14 may be fitted. This fit can be selected so that, on the one hand, the mounting means 14 is releasable and, on the other, a secure seating is assured. A releasable latching type of connection may also be selected. To the mounting means 14 a funnel 16 may be connected, for example. This permitts the position of the anchor 12 to be computed from the length of the needle 14 from mechanically sensing the funnel 16 and the orientation of the needle 14 when the anchor is configured as a marker.

As an alternative (not shown) an external marker may be secured to the mounting means 14 outside of the skin 24. In this arrangement, depending on the nature of the method of examination or analysation selected (CT, x-ray imaging or nuclear magnetic resonance tomography) a suitable marker can be connected to the mounting means 14. The positions of the external markers can be established by any of the "teach-in" techniques.

The mounting means 14 may be inserted in the head by simple means prior to an analytical scan and provided with a suitable external marker, e.g., a ball of titanium. After scanning, the mounting means 14 can be simply released from the anchor so that the part of the body to be examined can be disinfected with no problem prior to the operation. To produce a relationship to the corporeal data obtained from the analytical scan the mounting means 14 is then returned in place prior to the operation and provided with a suitable external marker (e.g. a reflector ball). Since the positions of these external markers agree with the positions of the external markers of the analytical scan, a direct assignment to the data obtained from the analytical scan is possible. Referencing between the external markers during the operation and the instrument is then done via the instrument position determining means.

If the anchors of the anchoring means are also configured as markers, having to insert the insert 14, 16 in subsequent examinations can be eliminated. It is sufficient in comparing the various examination results of the three-dimensional analytical scans that the internal markers (in this case the anchors) are always present in the same location. As an alternative the anchors may also be formed from a plastics material, for example, in which marker balls (e.g. balls of titanium) are incorporated.

I claim:

1. A method of localizing an instrument relative to three dimensional corporeal data, particularly for stereotaxis, comprising the following steps:
    a) connecting an internal marker means fixedly to a body to define an intracorporeal, spatial reference system,
    b) implementing an analytical scan of the body including said internal marker means to determine the positions of said three-dimensional corporeal data obtained from said analytical scan in said intracorporeal reference system defined by said internal marker means,
    c) implementing a referencing step, whereby position and orientation of said intracorporeal reference system defined by said internal marker means relative to an extracorporeal reference system defined by an external marker means is determined and said external marker means is located outside of the body in a fixed spatial relationship to the body,
    d) determining the position and orientation of an instrument in said extracorporeal reference system by means of said external marker means and an instrument marker means attached to said instrument, and
    e) computing from the position and orientation of the instrument in said extracorporeal reference system the position and orientation of said instrument in said intracorporeal reference system via the relationship between said intracorporeal and said extracorporeal reference system known from step c), wherein said referencing step comprises a reference scan of said internal marker means and said external marker means, and wherein said external marker means comprises a first external marker means and a second external marker means, the relative spatial positions of which to each other define respective first and second extracorporeal reference systems which rest one in the other, said first marker means being scannable by said referencing scan to thus define the relative position of said intracorporeal reference system to said first extracorporeal reference system, and said second marker means is scannable by an instrument position determining means so as to define the position and orientation of said instrument in said second reference system.

2. The method as set forth in claim 1, wherein said internal marker means is implanted subcutaneously.

3. The method as set forth in claim 2, wherein said internal marker means is secured to a skeleton.

4. The method as set forth in claim 1, wherein said internal marker means consist of at least three internal markers for establishing an intracorporeal, spatial reference system.

5. The method as set forth in claim 4, wherein said internal markers are globular.

6. The method as set forth in claim 4, wherein said internal markers are made of a material which is traceable both in analytical scanning and in reference scanning.

7. The method as set forth in claim 6, wherein said internal markers are made of titanium.

8. The method as set forth in claim 1, wherein the relative position of said first external marker means to said second external marker means is defined by means of a spacer mounting means transparent to x-ray radiation.

9. The method as set forth in claim 1, wherein said referencing scan is done by at least two x-ray images from different, known directions, whereby all-in-all at least three positions defining said first extracorporeal reference system of said first external marker means together with said internal marker means are scanned.

10. The method as set forth in claim 1, wherein said referencing scan is carried out by at least two x-ray images from different directions not necessarily precisely known, whereby for each x-ray image at least three positions defining said first extracorporeal reference system of said first external marker means together with said internal marker means are scanned.

11. The method as set forth in any of the claim 8, wherein said first external marker means comprises metallic markers joined by glass-like material.

12. The method as set forth in claim 11, wherein said metallic markers form copper frames, one copper frame each being encapsulated in a block of resinous material, and the blocks being arranged so that for each x-ray image one copper frame located ahead of the body in the imaging direction, and one copper frame located behind the body in the imaging direction are scanned together with said internal marker means, said second external marker means being secured to said blocks.

13. The method as set forth in any of the claim 1, wherein said second external marker means as well as said instrument marker means comprise optical infra-red reflectors and said instrument position determining means comprises at least three infra-red cameras as well as emitting infra-red radiation.

14. The method as set forth in any of the claim 1, wherein said internal marker means is implanted subcutaneously.

15. The method as set forth in claim 13, wherein said internal marker means is secured to a skeleton.

16. A marker device for defining a corporeal reference system comprising
    a) an anchoring means implantable subcutaneously and securable to a skeleton,
    b) an insert comprising a mounting means and marker means, c) said mounting means being releasably securable in said anchoring means and d) said marker means being releasably connectable to said mounting means outside of the body.

17. The marker device as set forth in claim 16, wherein said mounting means comprises a perforation means to permit penetration of the skin for simply securing said mounting means.

18. The marker device as set forth in claim 16, wherein said mounting means is configured to receive globular, replaceable markers at one of its ends.

19. The marker device as set forth in any of the claim 16, wherein said anchoring means comprises an internal marker means.

20. A device for referencing an extracorporeal reference system to an intracorporeal reference system, comprising a) a first external marker means including first external markers, the position of which is scannable by x-ray images, the first external markers defining a first extracorporeal reference system by their known position relative to each other, b) a spacer mounting means which is transparent for x-ray radiation and c) a second external marker means which by means of said spacer mounting means is mounted in a known, fixed position relative to said first external marker means and includes second external markers, the position of which is determinable by an instrument position determining means, the second external markers defining by their relative position to each other a second extracorporeal reference system, which rests in said first extracorporeal reference system.

21. The device as set forth in claim 20, wherein said first external markers are arranged so that for at least two x-ray images accomplished in differing directions at least three of said first external markers each are scanned, which define said extracorporeal reference system.

22. The device as set forth in claim 21, wherein the at least three markers scanned by an x-ray image are distributed opposed to each other along a periphery of an object to be examined.

\* \* \* \* \*